(12) United States Patent
Cohen et al.

(10) Patent No.: US 7,947,028 B2
(45) Date of Patent: May 24, 2011

(54) DIAPER WITH UMBILICAL FEATURE

(75) Inventors: Jason C. Cohen, Appleton, WI (US);
Kusum Gosain, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1541 days.

(21) Appl. No.: 11/084,317

(22) Filed: Mar. 18, 2005

(65) Prior Publication Data

US 2006/0212013 A1 Sep. 21, 2006

(51) Int. Cl.
*A61F 13/15* (2006.01)

(52) U.S. Cl. ......... 604/385.09; 604/385.01; 604/385.24; 604/385.31; 604/387; 604/389; 604/391; 604/394

(58) Field of Classification Search ............. 604/385.09, 604/385.01, 385.24, 385.31, 387, 389, 391, 604/394

See application file for complete search history.

(56) References Cited

U.S. PATENT DOCUMENTS

| | | | |
|---|---|---|---|
| 2,525,396 A | 10/1950 | Brennan |
| 2,684,677 A | 7/1954 | Pinney |
| 2,738,789 A | 3/1956 | Foxworthy |
| 3,141,461 A | 7/1964 | Farris |
| 3,623,488 A | 11/1971 | Nakayama |
| 4,230,113 A | 10/1980 | Mehta |
| 4,675,015 A | 6/1987 | Brown |
| 4,769,023 A | 9/1988 | Goebel et al. |
| 4,795,452 A | 1/1989 | Blaney et al. |
| 4,801,298 A | 1/1989 | Sorenson et al. |
| D311,582 S | 10/1990 | Gilchrist |
| 5,064,421 A | 11/1991 | Tracy |
| D334,978 S | 4/1993 | Rutherford |
| D341,422 S | 11/1993 | Cosentino |
| 5,295,986 A | 3/1994 | Zehner et al. |
| 5,306,267 A | 4/1994 | Hahn et al. |
| 5,318,555 A | 6/1994 | Siebers et al. |
| 5,358,500 A | 10/1994 | Lavon et al. |
| 5,366,453 A | 11/1994 | Zehner et al. |
| 5,406,964 A | 4/1995 | Calleja |
| 5,489,282 A | 2/1996 | Zehner et al. |
| 5,599,338 A | 2/1997 | Enloe |
| 5,669,897 A | 9/1997 | Lavon et al. |
| 5,707,364 A | 1/1998 | Coates |
| 5,814,037 A | 9/1998 | Coates |
| 5,836,930 A | 11/1998 | Lantz et al. |
| D403,400 S | 12/1998 | Bernard et al. |
| D403,401 S | 12/1998 | Bernard et al. |
| D403,402 S | 12/1998 | Dreier et al. |
| 6,110,157 A | 8/2000 | Schmidt |
| D452,315 S | 12/2001 | Coates |
| 6,423,047 B1 | 7/2002 | Webster |
| 6,482,194 B1 | 11/2002 | Putzer |
| 6,626,879 B1 | 9/2003 | Ashton et al. |

FOREIGN PATENT DOCUMENTS

DE 198 54 123 5/2000

(Continued)

*Primary Examiner* — Jacqueline F. Stephens
(74) *Attorney, Agent, or Firm* — David J. Arteman (57) ABSTRACT

A diaper has an unfastened condition and a fastened condition. The diaper has a front portion, a back portion and a fastener system. The fastener system is adapted to join the back portion to the front portion thereby transitioning the diaper from the unfastened condition to the fastened condition. The diaper is adapted to provide an umbilical relief area when in the fastened condition without tearing or folding the front waist edge. The diaper does not have an umbilical notch when in the unfastened condition.

20 Claims, 11 Drawing Sheets

FOREIGN PATENT DOCUMENTS

| | | |
|---|---|---|
| EP | 0 155 636 A2 | 9/1985 |
| EP | 0 721 770 A2 | 7/1996 |
| FR | 2 604 867 A1 | 4/1988 |
| GB | 1 133 502 A | 11/1968 |
| JP | 03-236839 A | 10/1991 |
| WO | WO 97/18785 | 5/1997 |
| WO | WO 03/009792 A1 | 2/2003 |
| WO | WO 2004/060230 | 7/2004 |

DIAPER WITH UMBILICAL FEATURE

BACKGROUND OF THE INVENTION

Absorbent articles, such as disposable diapers, have generally included topsheets, backsheets, and absorbent structures. Some diapers specifically designed for newborn children have further included V-shaped or U-shaped notches cut into the front waist section of the diaper to minimize contact with the umbilical cord and/or navel of newborn children. Such diapers require additional processing and can slow production and/or negatively impact quality.

Other diapers designed for newborn children have included various perforations and separable panels to minimize contact with the umbilical cord region of newborns. However, these solutions have required additional processing steps to provide the desired umbilical feature. Yet other diapers have required a part of the diaper be removed by the caregiver to utilize the umbilical feature. In these designs, the inconvenience of removing and disposing of a separate part may be less desirable. Some diapers have required additional manipulation by the caregiver, such as by folding the front edge, to utilize the umbilical feature. In these designs, the inconvenience of manipulating the diaper with a wiggling baby may not be desirable.

As a result, there is a continued need for disposable diapers, particularly useful with newborns, to include an umbilical feature that does not require additional processing steps, additional manipulation by the caregiver, or the disposal of removable parts.

SUMMARY OF THE INVENTION

In response to the discussed need, the present invention provides diapers with umbilical features. In one embodiment, a diaper has an unfastened condition and a fastened condition. The diaper has a front portion, a back portion and a fastener system. The fastener system is adapted to join the back portion to the front portion thereby transitioning the diaper from the unfastened condition to the fastened condition. The diaper is adapted to provide an umbilical relief area when in the fastened condition without tearing or folding the front waist edge. The diaper does not have an umbilical notch when in the unfastened condition.

In a second embodiment, a diaper has an unfastened condition, a fastened condition and a longitudinal centerline. The diaper includes a front portion and a back portion. The front portion has a straight front waist edge at the longitudinal centerline and at least one front fastener. The back portion has at least one back fastener. The at least one back fastener is adapted to join with the at least one front fastener thereby transitioning the diaper from the unfastened condition to the fastened condition. The diaper has a fastened offset of at least 15 mm.

In a third embodiment, a diaper has an unfastened condition and a fastened condition. The diaper includes a front portion, a back portion and a fastener system. The fastener system is adapted to join the back portion to the front portion thereby transitioning the diaper from the unfastened condition to the fastened condition. The front portion has a front waist edge and a front fastener having a front fastener offset of less than 30 mm. The back portion has a back waist edge and a pair of back fasteners having a back fastener offset of at least 50 mm.

In various embodiments, the diaper may also have a longitudinal centerline. The fastener system may include a front fastener and a pair of back fasteners. The back fasteners may be adapted to join with the front fastener to transition the diaper from the unfastened condition to the fastened condition. The front portion may have a straight front waist edge at the longitudinal centerline.

In various embodiments, the diaper may have a fastened offset of at least 15 mm, of at least 20 mm, of at least 25 mm, or of at least 30 mm.

In various embodiments, the diaper may have at least one front fastener having a front fastener offset of less than 30 mm and at least one back fastener having a back fastener offset of at least 50 mm.

In various embodiments, the diaper may have at least one front fastener having a front fastener offset of less than 25 mm or of less than 20 mm.

In various embodiments, the diaper may have at least one back fastener having a back fastener offset of at least 60 mm or of at least 70 mm.

In various embodiments, the diaper may also have at least one stabilizer joined with the back portion and the back portion may have a back waist edge. The at least one stabilizer may be located proximate the back waist edge and adapted to minimize back waist edge rollover.

In various embodiments, the diaper may also have at least one stabilizer joined with the front portion and the front portion may have a front waist edge. The at least one stabilizer may be located proximate the front waist edge and adapted to minimize front waist edge rollover.

DETAILED DESCRIPTION OF THE DRAWINGS

The absorbent article of the present invention will be described in terms of a diaper adapted to be worn by infants, particularly newborns, about the lower torso. The diaper of the present invention is an improvement over the prior art diapers having umbilical features.

The diapers of the present invention minimize contact with the umbilical cord and/or navel without requiring the caregiver to tear off a portion of the product or fold the waist edge because alignment of the fasteners of the diaper of the present invention creates the umbilical feature. The diaper of the present invention has an easy to use umbilical feature and does not require disposal of a removable piece. The diapers of the present invention can also be more easily manufactured because additional processing steps, such as perforating a notch or cutting and removing a notch are not required as in traditional diapers with umbilical features.

Figure 1:
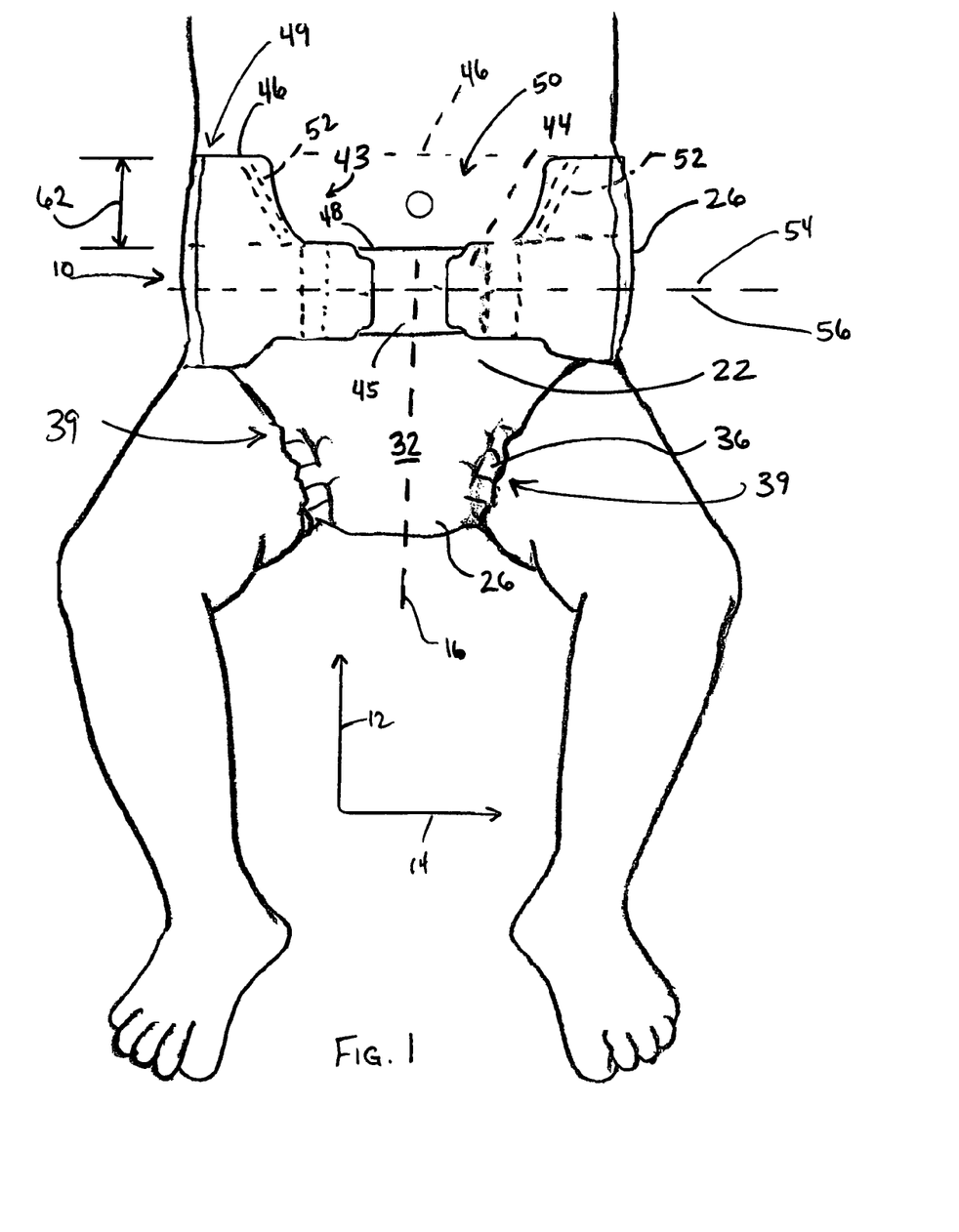
FIG. 1 representatively illustrates a perspective view of an exemplary diaper in a fastened condition about the waist and legs of an infant.
Figure 2:
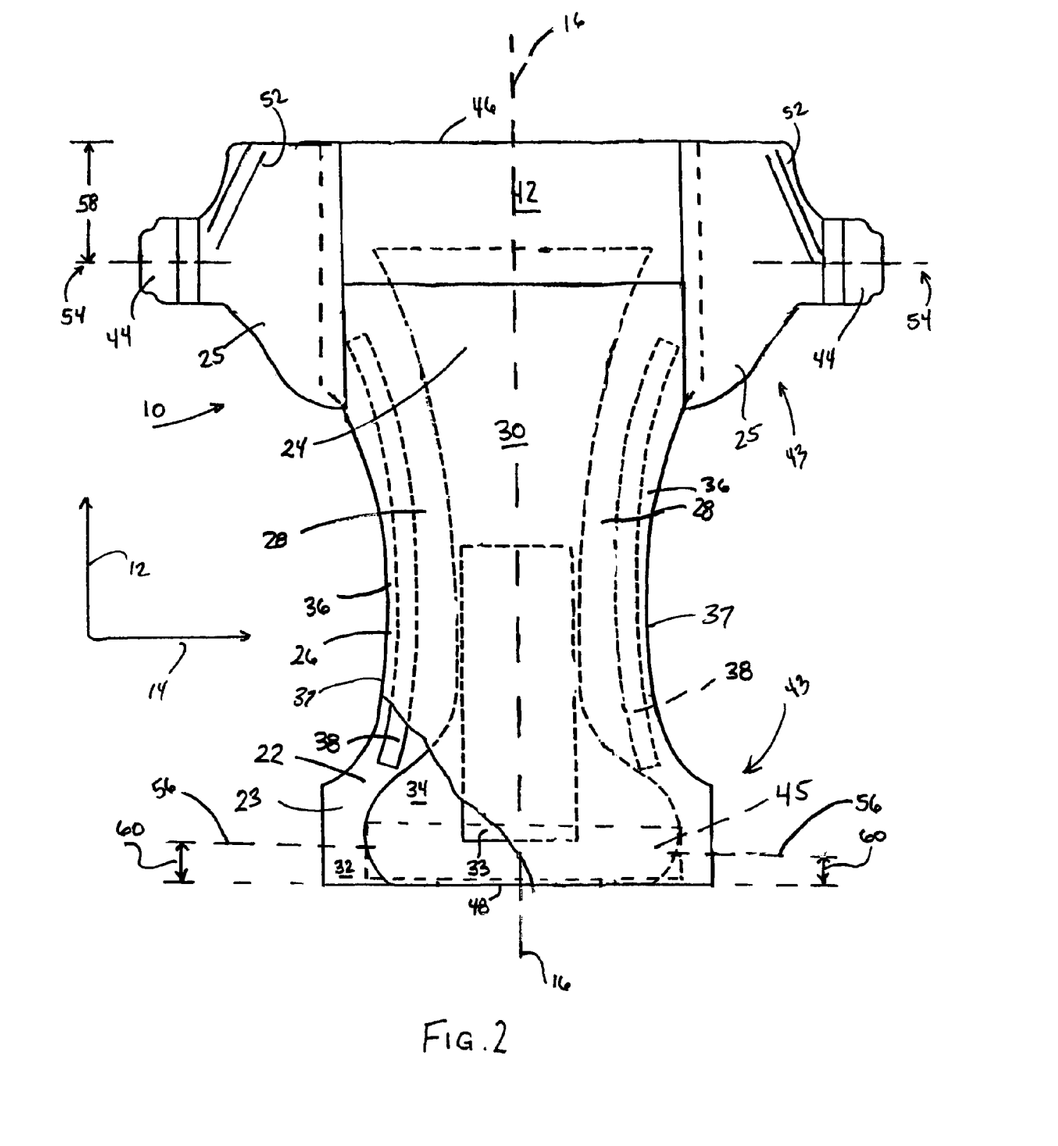
FIG. 2 representatively illustrates a partially cut away, top plan view of the diaper of FIG. 1 in a stretched and laid flat condition with the surface of the diaper that contacts the skin of the wearer facing the viewer.
Figure 3:
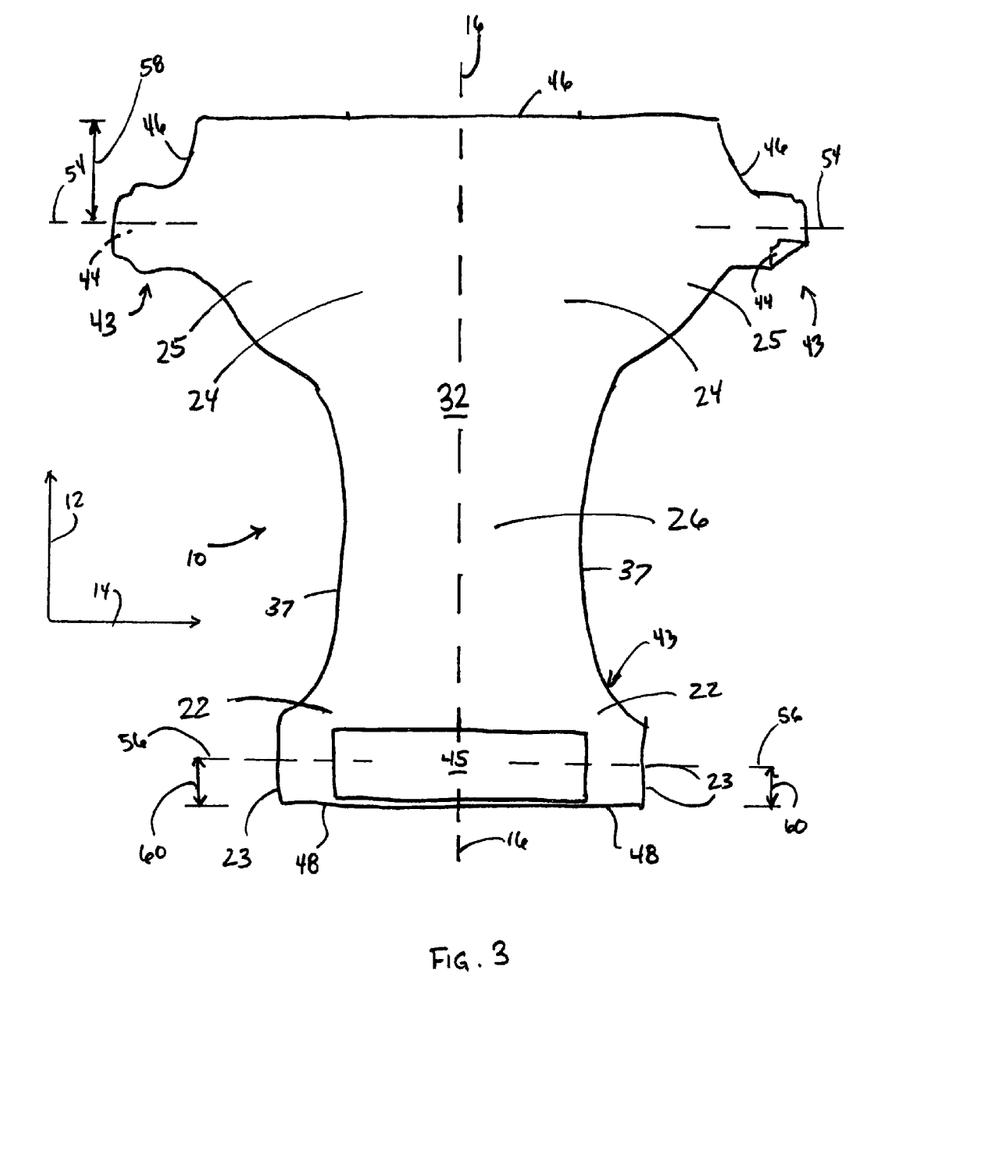
FIG. 3 representatively illustrates a top plan view of the diaper of FIGS. 1 and 2 in a stretched and laid flat condition with the surface of the diaper that contacts the clothes of the wearer facing the viewer.

FIG. 1 representatively illustrates a diaper 10 of the present invention fastened about the waist of an infant. The diaper 10 is said to be in the fastened condition. FIGS. 2 and 3 representatively illustrate the diaper 10 of FIG. 1 in an unfastened condition. The surface of the diaper which contacts the wearer is facing the viewer in FIG. 2. The surface of the diaper which contacts the wearer's clothes is facing the viewer in FIGS. 1 and 3. The diaper 10 has a longitudinal direction 12 and a lateral direction 14. The diaper 10 has a longitudinal centerline 16 depicted as a dashed line.

Referring now to FIGS. 2 and 3, the diaper 10, in the longitudinal direction 12, defines a front portion 22, a back portion 24, and a crotch portion 26 connecting the front portion 22 and the back portion 24. The diaper 10 includes a bodyside liner 30, an outer cover 32 and an absorbent core 34 located between the bodyside liner 30 and the outer cover 32. The front portion 22 may include, at least partially, one or more front ears 23. The back portion 24 may include, at least partially, one or more back ears 25. The front ears 23 and/or the back ears 25 may be formed from extensions of the bodyside liner 30, the outer cover 32, combinations of both the bodyside liner 30 and the outer cover 32, or by the addition of one or more separate components as is known in the art.

The diaper 10 also includes a fastener system 43. The fastener system 43 includes one or more back fasteners 44 and one or more front fasteners 45. Portions of the fastener system 43 may be included in the front portion 22, back portion 24, or both. The fastener system 43 is adapted to secure the diaper 10 about the waist of a wearer and maintain the diaper 10 in place during use. In some embodiments, the diaper 10 may also include one or more stabilizers 52. The diaper 10 may also include a surge portion 33 joined to the absorbent core 34 and/or bodyside liner 30.

As used herein, reference to a front portion refers to that part of the diaper which is generally located on the front of a wearer when in use. Reference to the back portion refers to the portion of the diaper generally located at the back of the wearer when in use, and reference to the crotch portion refers to that portion which is generally located between the legs of the wearer when in use.

The crotch portion 26 has opposite longitudinal side portions 28 which may include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 may be elasticized by a pair of leg elastics 38. The diaper 10 may further include a front waist elastic 40 and/or a back waist elastic 42.

The back portion 24 may have a straight back waist edge 46, an arcuate back waist edge 46, a notched back waist edge 46, a convex or concave back waist edge 46, or a back waist edge 46 cut in any other shapes. The front portion 22 generally has a straight front waist edge 48 proximate the longitudinal centerline 16 of the product. As used herein, the term "straight" refers to edges that are substantially free from curves, bends, angles, notches or irregularities. Alternatively, in particular embodiments, the front waist edge 46 may have one or more notches, protrusions, steps, or the front waist edge 46 may have an irregular shape.

The bodyside liner 30 of the diaper 10, as representatively illustrated in FIG. 2, suitably presents a body-facing surface which is intended to be worn adjacent the body of the wearer and is compliant, soft feeling and nonirritating to the wearer's skin. Further, the bodyside liner 30 may be less hydrophilic than the absorbent core 34 and may be sufficiently porous to be liquid permeable. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 may be a polypropylene spunbond. The bodyside liner 30 is suitably employed to help isolate the wearer's skin from fluids held in the absorbent core 34.

The outer cover 32 of the diaper 10, as representatively illustrated in FIG. 3, suitably presents a garment facing surface which is intended to be worn adjacent the clothing of the wearer. The outer cover 32 may be a polyethylene film. Alternative constructions of the outer cover 32 may comprise a woven or non-woven fibrous web layer which has been totally or partially constructed or treated to impart a desired level of liquid impermeability to selected regions of the backsheet that are adjacent or proximate the absorbent core 34. For example, a clothlike backsheet may be composed of polypropylene spunbond fabric which is laminated and thermally bonded to a stretch-thinned polypropylene film. Outer cover 32 may optionally include a micro-porous, "breathable" material which permits vapors to escape from diaper 10 while still preventing liquid exudates from passing through. For example, the outer cover 32 may be composed of a microporous polymer film or a nonwoven fabric which has been coated or otherwise treated to impart a desired level of liquid impermeability. The outer cover 32 can also be embossed or otherwise provided with a matte finish to exhibit a more aesthetically pleasing appearance. The size of outer cover 32 is typically determined by the size of diaper 10 and the exact diaper design selected.

The bodyside liner 30 and outer cover 32 are generally joined in facing relationship with the absorbent core 34 located therebetween. The bodyside liner 30 and the outer cover 32 may be joined to each other around the outer periphery of the diaper 10 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 36 are suitably formed by portions of the outer cover 32, and/or bodyside liner 30, which extend beyond the longitudinal sides of the absorbent core 34. Alternatively, the leg cuffs 36 can be formed from separate materials joined to the outer cover 32 and/or bodyside liner 30. In some embodiments, the leg cuffs 36 may have an arcuate shape resulting from a leg cut out 37. In other embodiments, the leg cuffs 36 may have a generally straight leg cut out 37.

The leg elastics 38, front waist elastics 40, back waist elastics 42, and other elastic materials may also be provided to draw and hold the diaper 10 against the legs and/or waist of the infant to improve gasketing and minimize leakage. Materials suitable for use in forming leg elastics 38 and/or waist elastics 40 and 42 are known to those skilled in the art. Exemplary of such materials are strands or ribbons of a polymeric, elastomeric material which are adhered to the diaper 10 in a stretched position, or which are joined to the diaper while the diaper is pleated, such that elastic constrictive forces are imparted to the diaper 10. The leg elastics 38 and waist elastics 40 and 42 may have any configuration which provides the desired performance. The leg elastics 38 may be generally straight or optionally curved to more closely fit the contours of the legs and buttocks of the wearer and better contain bodily exudates. The leg elastics 38 and waist elastics 40 and 42 may be joined to the diaper 10 in any of several ways which are well known to those skilled in the art. For example, the elastics may be joined to the diaper 10 by ultrasonic bonding, thermal bonding, adhesive bonding, and the like, and combinations thereof.

The front ears 23 and/or the back ears 25 are suitably formed by portions of the outer cover 32, and/or bodyside liner 30, which extend beyond the longitudinal sides of the absorbent core 34. For example, in FIG. 2, the front ears 23 are illustrated as portions of both the outer cover 32 and the bodyside liner 30. Alternatively, the front ears 23 and/or back ears 25 could be formed from separate materials which are joined to the outer cover 32 and/or bodyside liner 30. For example, in FIG. 2, the back ears 25 are illustrated as separate pieces of material joined to the bodyside liner 30. The front ears 23 and/or back ears 25 may further include stabilizers 52 to reduce or minimize rollover of the back waist edge 46 and/or the front waist edge 48.

The front ears 23 and/or the back ears 25 of the diaper may comprise one or more materials joined together to form a composite ear as is well known in the art. One or more of the materials may be elastomeric. Elastomeric ears can be formed from any type of an elastomeric material capable of performing as described herein. Generally, the elastomeric material will be stretchable in at least one direction. Preferably, the elastomeric material will be stretchable in two directions. When the elastomeric material is stretchable in a single direction, the stretch direction of the elastomeric material will preferably be oriented so as to provide elastomeric forces which tend to pull the front and back portions of the diaper towards one another such that the diaper is maintained about the waist of a wearer.

The elastomeric material may be an inherently elastomeric material, that is, one which is formed in an elastomeric state, or may be rendered elastomeric through processing subsequent to formation. For example, the elastomeric material may be heat or pressure activated. In particular embodiments of the invention, portions of the ears may comprise an elastomeric material, such as a stretch-bonded-laminate (SBL) material, a neck-bonded-laminate (NBL) material, an elastomeric film, an elastomeric foam material, or the like.

The fastener system 43 provides a means for securing the diaper 10 on the wearer. The fastener system 43 includes at least one back fastener 44 and at least one front fastener 45. In some embodiments, the fastener system 43 includes two back fasteners 44 and one front fastener 45. The back fasteners 44 define a back fastener centerline 54, depicted as a dashed line. The back fastener centerline 54 is remote from the back waist edge 46 by a back fastener offset distance 58 as measured at the longitudinal centerline 16. In some embodiments, the back fastener centerline 54 is generally parallel with the lateral direction 14. In other embodiments, the back fastener centerline 54 is non-parallel with the lateral direction 14. In various embodiments, the back fastener offset distance 58 may be at least 40 mm, at least 45 mm, at least 50 mm, at least 55 mm, at least 60 mm, at least 65 mm, or at least 70 mm. In some embodiments, the back fastener offset distance 58 may be greater than 75 mm.

The front fasteners 45 define a front fastener centerline 56. The front fastener centerline 60 is remote from the front waist edge 48 by a front fastener offset distance 60 as measured at the longitudinal centerline 16. In some embodiments, the front fastener centerline 56 is generally parallel with the lateral direction 14. In other embodiments, the front fastener centerline 56 is non-parallel with the lateral direction 14. In various embodiments, the front fastener offset distance 60 is less than 40 mm, less than 35 mm, less than 30 mm, less than 25 mm, or less than 20 mm.

In some embodiments, the back fasteners 44 may be joined to the back portion 24, the back ears 25 or both and the front fasteners 45 may be joined to the front portion 22, the front ears 23, or both. The back fasteners 44 may be one or more discrete pieces of material joined to the diaper 10 and adapted to align with and work in conjunction with the front fasteners 45, which may be one or more discrete pieces of material joined to the diaper 10. For example, the front fastener 45 may be a piece of loop material joined with the outercover 32 in the front portion 22 and configured to engage hook-type back fasteners 44 when the diaper 10 is wrapped about the waist and legs of a user.

Alternatively, the front fasters 45 may include portions of the outercover 32, the bodyside liner 30, or both and be configured to engage hook-type back fasteners 44. For example, the outercover 32 may be configured to be a nonwoven material suitable for engagement with hook materials. In such an embodiment, hook-type fasteners 44 may be located at the back ear 25 and wrapped around the waist of the wearer. The hook-type fasteners 44 may then be engaged directly with the nonwoven outercover 32 to join the back portion 24 with the front portion 22 and secure the diaper 10 about the waist of the wearer. In such embodiments, the front fastener centerline 56 would be the lateral centerline of the front ear 23. The front ear 23, in these embodiments, is defined as the region spanning from the front waist edge 48 to the beginning of the leg cut out 37.

In some embodiments, the front fastener 45 may include graphics guiding a user to place the back fasteners 44 in a particular location. In such embodiments, the front fastener centerline 56 is determined relative to the graphics. In some embodiments, the front fasteners 45 may include hook-type fasteners and the back fasteners 44 may include one or more complementary loop-type fasteners. In various embodiments, the back fasteners 44 and front fasteners 45 may comprise any suitable materials adapted to join the back portion 24 to the front portion 22 of the diaper 10 thus securing the diaper about the waist of a wearer. Suitable fastening materials include mechanical fasteners, hook and loop materials, adhesives, adhesive tapes, cohesives, snaps, buttons, latches, hooks, and the like, and combinations thereof. In some embodiments both the front portion 22 and the back portion 24 may include dual fasteners as is known in the art. In embodiments including dual fasteners, the fastener system 43 may include first back fasteners having first back centerlines adapted to align with first front fasteners having first front fastener centerlines and second back fasteners having second back centerlines adapted to align with second front fasteners having second front fastener centerlines.

In various embodiments, the stabilizers 52 may include one or more additional elements joined to the diaper 10. For example, the stabilizers 52 may include resilient materials, elastomeric materials, adhesives, plastics, or any other rigid or semi-rigid material or materials adapted to provide stability. Alternatively, the stabilizers 52 may be provided by thermally deforming one or more of the bodyside liner 30, outercover 32, front waist elastic 40, back waist elastic 42, or back ears 25.

The absorbent core 34 is positioned between the bodyside liner 30 and the outer cover 32 to form the diaper 10. The absorbent core 34 is generally conformable and capable of absorbing and retaining body exudates. The absorbent core 34 may include superabsorbent material, staple fibers, binder fibers, and the like, and combinations thereof as is known in the art. The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the diaper. The absorbent core 34 is depicted herein as extending proximate the front waist edge 48. Those skilled in the art will appreciate that the length and position of the absorbent core 34 may be selected such that the absorbent core 34 is more or less removed from the front waist edge 48 as desired for the intended use of the diaper.

In various embodiments, the surge portion 33 serves to quickly collect and temporarily hold discharged fluids and then to eventually release the fluids into the absorbent core 34. Various woven and nonwoven materials can be used to construct the surge portion 33. For example, the surge portion 33 may be a layer of a spunbonded or meltblown web of polyolefin fibers. The surge portion 33 may also be a bonded carded web of natural and synthetic fibers. The surge portion 33 may be a substantially hydrophobic material and, optionally, can be treated with a surfactant or otherwise to impart a desired level of wettability and hydrophilicity.

Containment flaps, not shown, may be connected to the bodyside liner or other components as is well known in the art. Suitable configurations of the containment flaps are described, for example, in U.S. Pat. No. 5,599,338 issued Feb. 4, 1997, to K. Enloe, the entirety of which is incorporated herein by reference where not contradictory.

Referring again to FIG. 1, the diaper 10 is shown in a fastened condition on an infant. The back fasteners 44 are joined to the back ears 25 in the back portion 24. The back ears 25 are wrapped around the infant's waist and hips and joined with the front fasteners 45 located in the front portion 22 to maintain the diaper generally in the position shown. The back fastener centerline 54 is generally aligned with and parallel to the front fastener centerline 56. Utilization of the diaper 10 having fastening system 43, with the centerlines 54 and 56 generally aligned and parallel, creates a waist opening 49, a pair of leg openings 39, and an umbilical relief area 50. The umbilical relief area 50 minimizes contact between the umbilical region of the infant and the diaper 10.

Utilization of the present diaper 10, having the fastening system 43, results in a fastened offset distance 62 between the back waist edge 46 and the front waist edge 48 as measured at the longitudinal centerline 16. The fastened offset distance 62 is a measure of the umbilical relief area 50 when the diaper 10 is in the fastened condition. More specifically, the position of the back fasteners 44 relative to the back waist edge 46 and the position of the front fastener 45 relative to the front waist edge 48 create the umbilical relief area 50 without the additional processing step of cutting or perforating an umbilical notch in the front waist edge 48. In various embodiments, the fastened offset distance 62 may be at least 30 mm, at least 35 mm, or at least 40 mm. In other embodiments, the fastened offset distance 62 may be greater than 45 mm.

Figure 4:
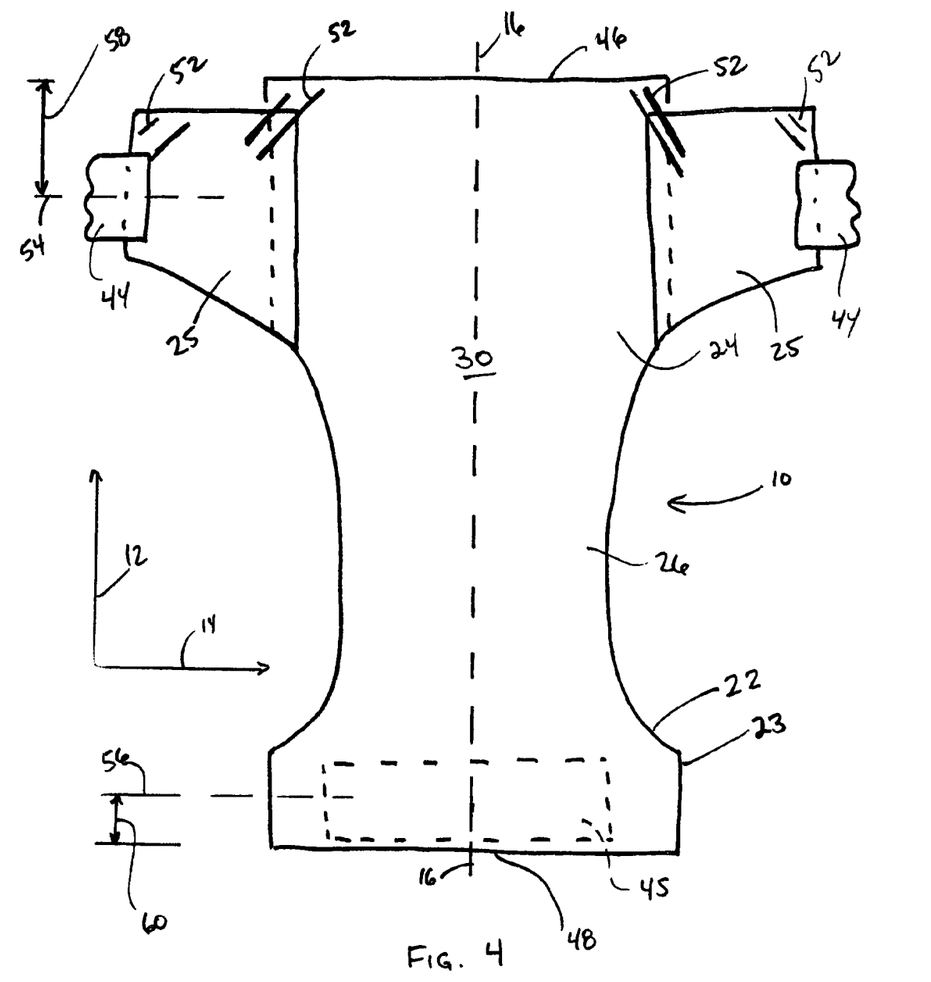
FIG. 4 representatively illustrates a top plan view of an exemplary diaper in a stretched and laid flat condition with the surface of the diaper that contacts the clothes of the wearer facing the viewer.
Figure 5:
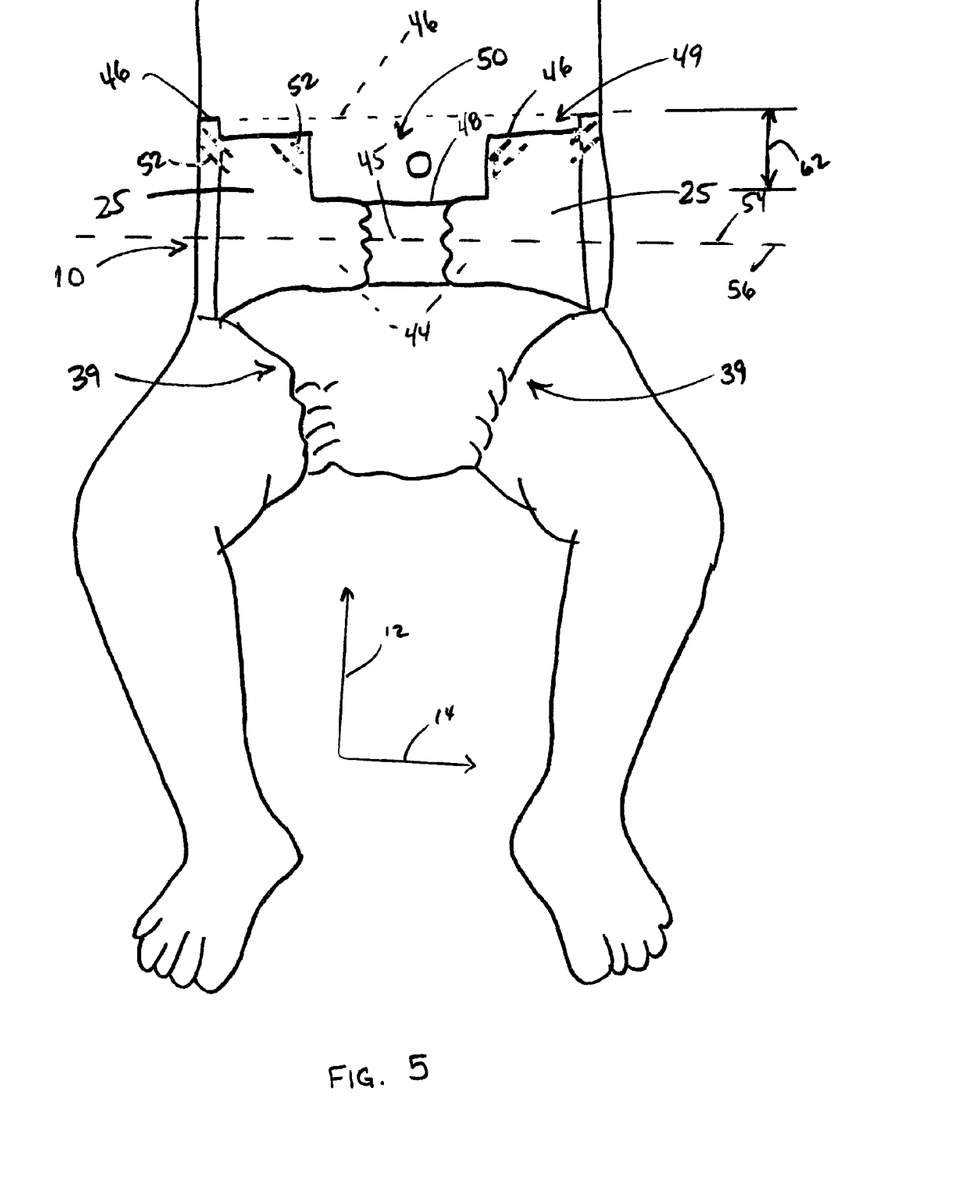
FIG. 5 representatively illustrates a perspective view of the diaper of FIG. 4 in a fastened condition about the waist and legs of an infant.

The shape of the umbilical relief area 50 can be altered by changing the shape of the front waist edge 48, the offset distance 62, the shape of the back ears 25, and/or the shape of the back fasteners 44. For example, FIG. 4 representatively illustrates an alternative embodiment of the present invention wherein a diaper 10 is shown in the unfastened condition and has back ears 25 with an alternative shape. FIG. 5 representatively illustrates the diaper 10 of FIG. 4 in the fastened condition about the waist of an infant. The back fasteners 44 are joined to the back ears 25 in the back portion 24. The back ears 25 are wrapped around the infant's waist and hips and joined with the front fastener 45 located in the front portion 22 to maintain the diaper 10 generally in the position shown. The back fastener centerline 54 is generally aligned with and parallel to the front fastener centerline 56. Utilization of the diaper 10, having fastening system 43, with the lateral centerlines 54 and 56 generally aligned and parallel, creates a waist opening 49, a pair of leg openings 39, and an umbilical relief area 50. The diaper 10 has a fastened offset distance 62. In the depicted embodiment, multiple stabilizers 52 are joined with the diaper 10 to minimize rollover of the back waist edge 46.

Figure 6:
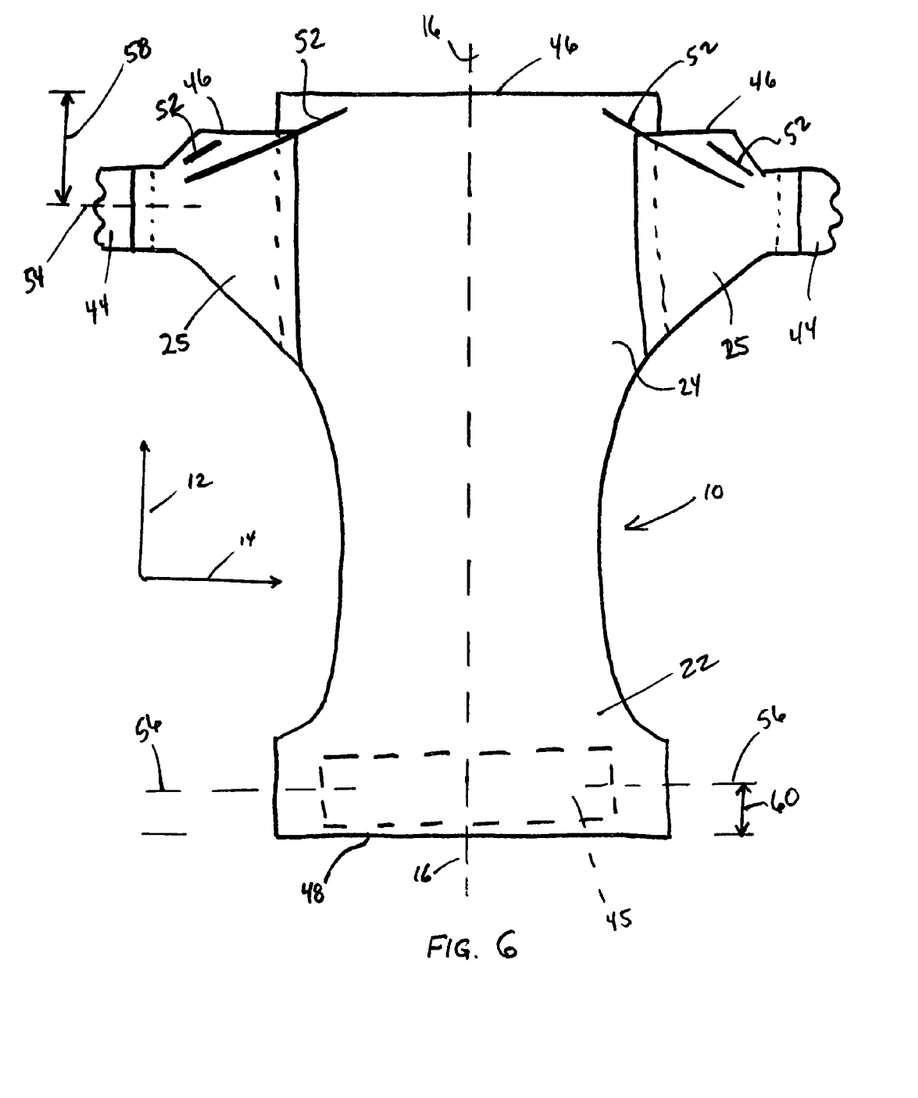
FIG. 6 representatively illustrates a top plan view of an exemplary diaper in a stretched and laid flat condition with the surface of the diaper that contacts the skin of the wearer facing the viewer.
Figure 7:
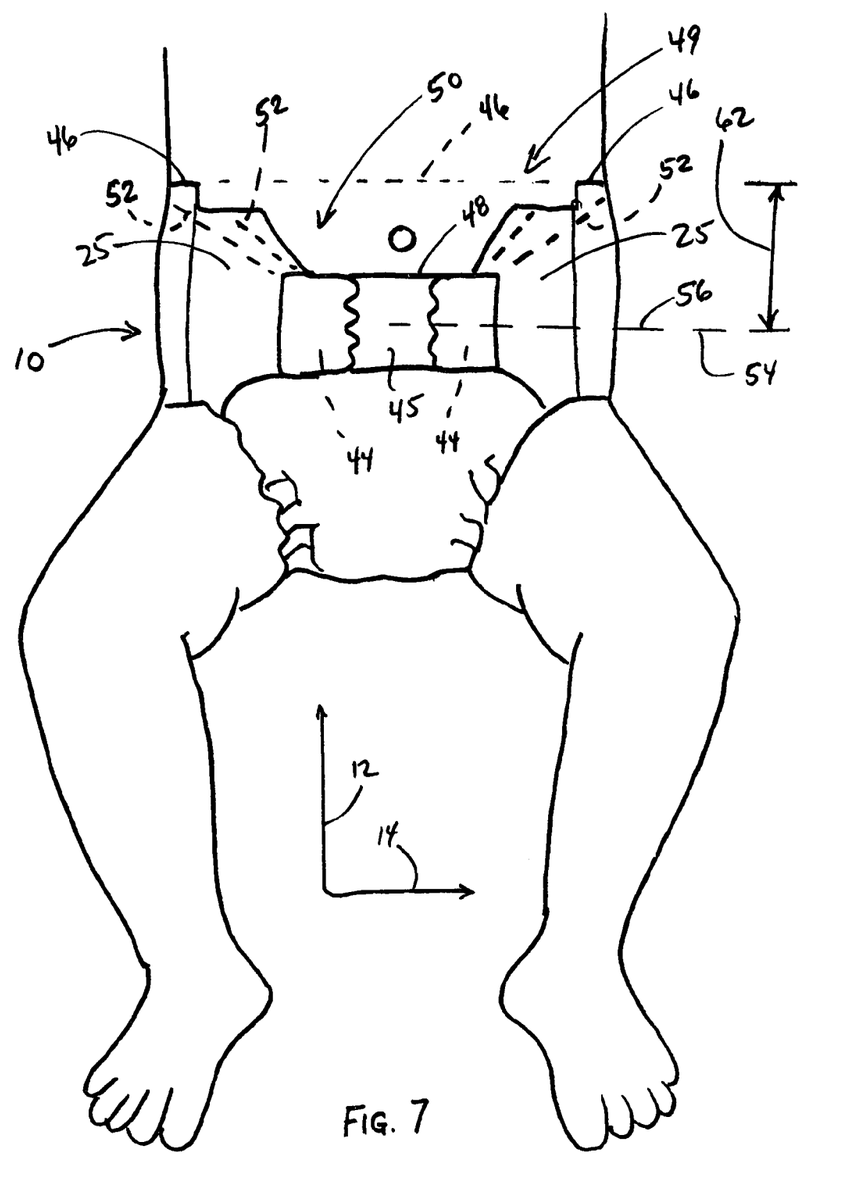
FIG. 7 representatively illustrates a perspective view of the diaper of FIG. 6 in a fastened condition about the waist and legs of an infant.

In another example, FIG. 6 representatively illustrates an alternative embodiment of the present invention wherein a diaper 10 is shown in the unfastened condition and has back ears 25 with an alternative shape. FIG. 7 representatively illustrates the diaper 10 of FIG. 6 in the fastened condition about the waist of an infant. The back fasteners 44 are joined to the back ears 25 in the back portion 24. The back ears 25 are wrapped around the infant's waist and hips and joined with the front fastener 45 located in the front portion 22 to maintain the diaper 10 generally in the position shown. The back fastener centerline 54 is generally aligned with and parallel to the front fastener centerline 56. Utilization of the diaper 10, having fastening system 43, with the centerlines 54 and 56 generally aligned and parallel, creates a waist opening 49, a pair of leg openings 39, and an umbilical relief area 50. The diaper 10 has a fastened offset distance 62. In the depicted embodiment, multiple stabilizers 52 are joined with the diaper 10 to minimize rollover of the back waist edge 46.

Figure 8:
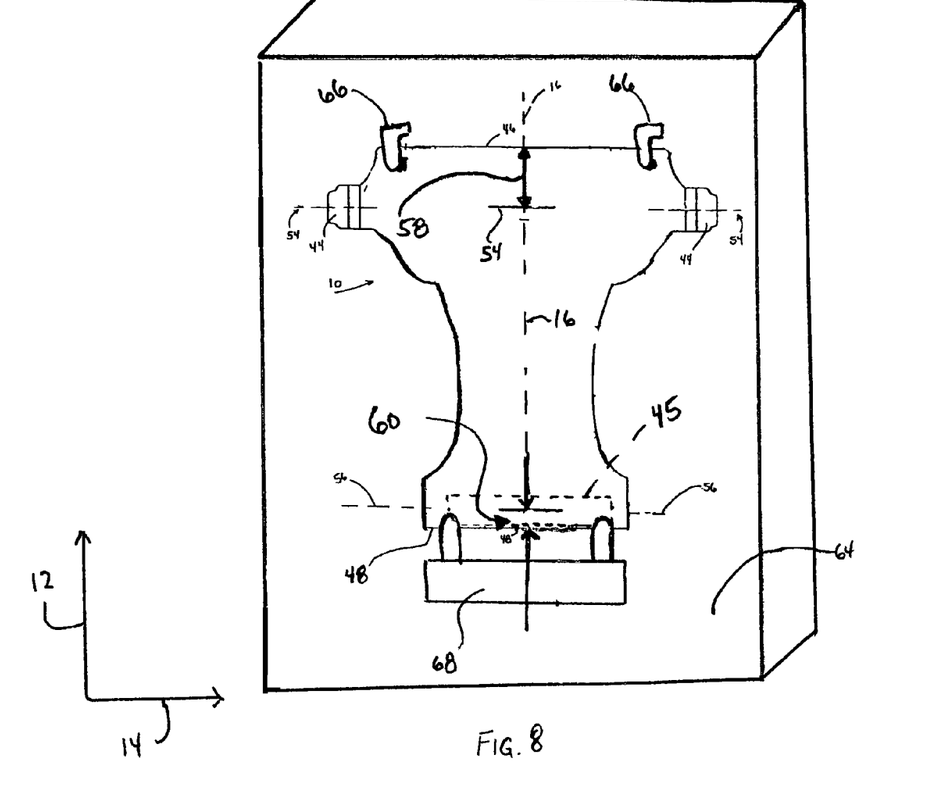
FIG. 8 representatively illustrates an exemplary diaper secured in a flat-out, uncontracted condition to measure the front fastener offset and/or the back fastener offset.
Figure 9:
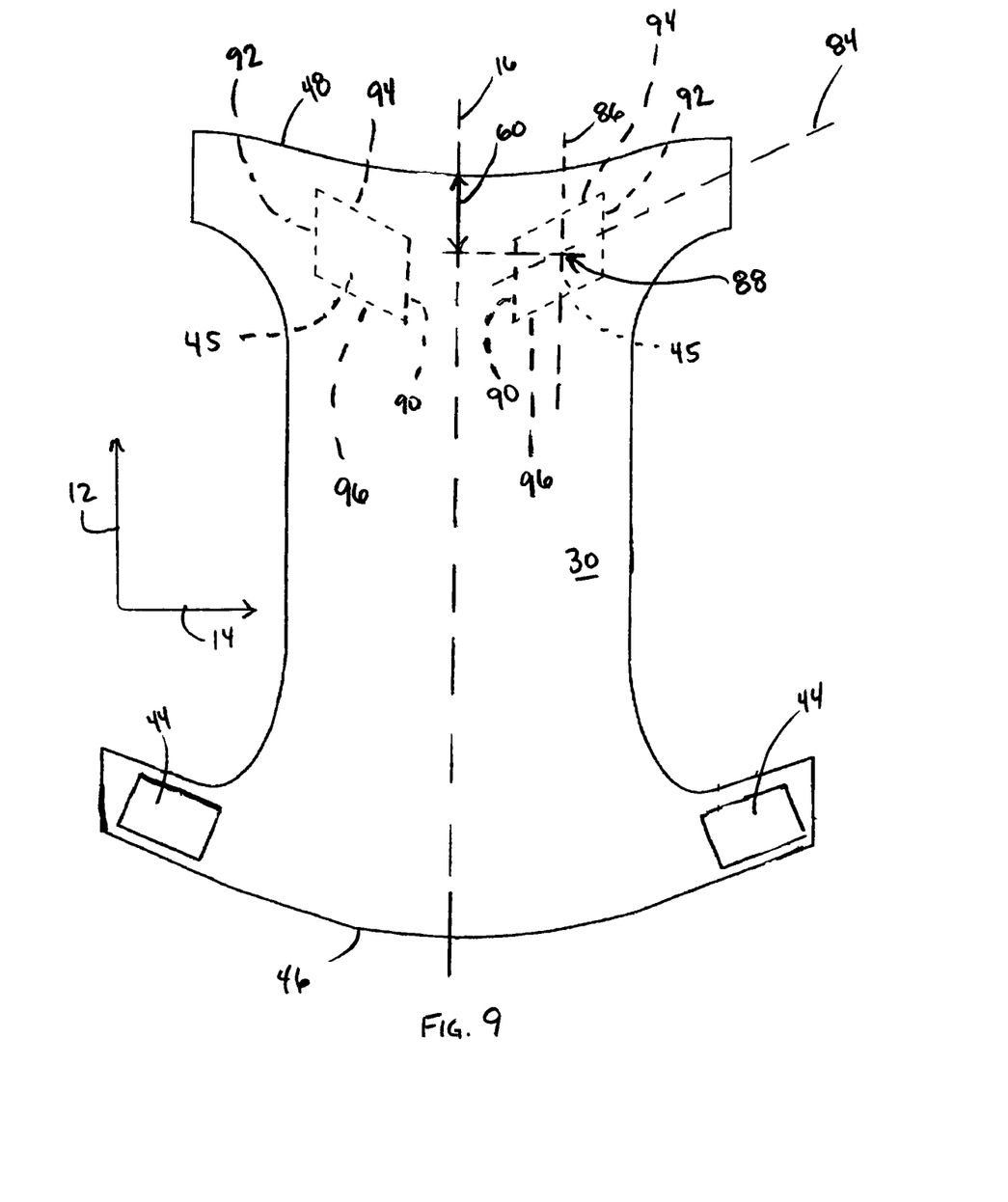
FIG. 9 representatively illustrates an exemplary diaper secured in a flat-out, uncontracted condition to measure the front fastener offset and/or the back fastener offset.

The fastened offset 62, back fastener offset 58 and the front fastener offset 60 can be measured by the following procedures. The diaper 10 is secured in the flat-out, uncontracted condition (i.e., with elastic induced contraction pulled out except in the front ears 23 and/or back ears 25 if elasticized), as illustrated in FIGS. 8 and 9. Use of a light board 64, clamps 66 and a weight 68 may facilitate this process. Alternatively or additionally the leg elastics 38 and/or flap elastics may be cut in several locations or removed to reduce or eliminate the retractive forces in the diaper 10.

Front Fastener Offset

In samples wherein the front fasteners 45 are generally parallel relative to the lateral direction 14, the diaper 10 is secured as illustrated in FIG. 8. Once the diaper 10 is secured as illustrated in FIG. 8, the front fastener centerline 56 is extended to the longitudinal centerline 16 of the diaper 10.

The front fastener offset 60 is the distance from the front fastener centerline 56 to the front waist edge 48 at the longitudinal centerline 16.

In samples wherein the front fasteners 45 are non-parallel relative to the lateral direction 14, the diaper 10 is secured in the flat-out, uncontracted condition as illustrated in FIG. 9. The front fasteners 45 have a proximal edge 90, a distal edge 92, a front edge 94 and a back edge 96. The proximal edge 90 is defined as the edge generally oriented towards and located closest to the longitudinal centerline 16. The distal edge 92 is generally opposite the proximal edge 90 and is remote from the longitudinal centerline 16. The front edge 94 is defined as the edge generally oriented towards the front waist edge 48. The back edge 96 is generally opposite the front edge 94 and is generally oriented towards the back waist edge 46. The front fasteners 45 define a first direction centerline 84 relative to the front edge 94 and the back edge 96. The front fasteners 45 define a second direction centerline 86 relative to the proximal edge 90 and the distal edge 92. The first direction centerline 84 and the second direction centerline 86 intersect at a midpoint 88. The midpoint 88 is extended parallel to the lateral direction 14 to the longitudinal centerline 16. The front fastener offset 60 is the distance from the extended midpoint 88 to the front waist edge 48 at the longitudinal centerline 16.

Figure 10:
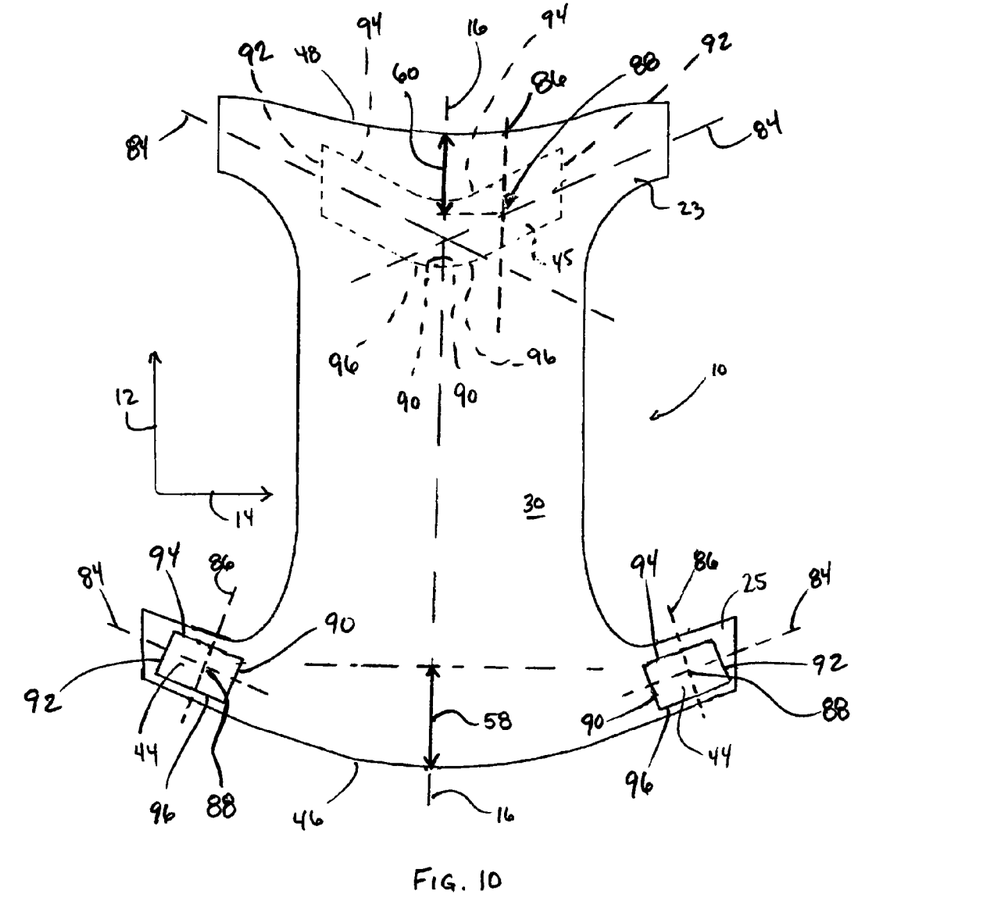
FIG. 10 representatively illustrates an exemplary diaper secured in a flat-out, uncontracted condition to measure the front fastener offset and/or the back fastener offset.

In samples wherein the front fastener 45 extends across the longitudinal centerline 16, such as illustrated in FIG. 10, the front fastener 45 is treated as if it were two front fasteners joined at the longitudinal centerline 16. As such, the proximal edge 90 is the longitudinal centerline 16. The front fasteners 45 have a first direction centerline 84 relative to front edge 94 and the back edge 96 and a second direction centerline 86 relative to the proximal edge 90 and the distal edge 92. The first direction centerline 84 and the second direction centerline 86 intersect at a midpoint 88. The midpoint 88 is extended parallel to the lateral direction 14 to the longitudinal centerline 16. The front fastener offset 60 is the distance from the extended midpoint 88 to the front waist edge 48 at the longitudinal centerline 16.

Back Fastener Offset

In samples wherein the back fasteners 44 are generally parallel relative to the lateral direction 14, the diaper 10 is secured as illustrated in FIG. 8 and the back fastener centerline 54 is extended to the longitudinal centerline 16 of the diaper 10. The back fastener offset 58 is the distance from the back fastener centerline 54 to the back waist edge 46 at the longitudinal centerline 16.

In samples wherein the back fasteners 44 are non-parallel relative to the lateral direction 14, the diaper 10 is secured in the flat-out, uncontracted condition as illustrated in FIG. 10. The back fasteners 44 have a proximal edge 90, a distal edge 92, a front edge 94 and a back edge 96. The proximal edge 90 is defined as the edge generally oriented towards and located closest to the longitudinal centerline 16. The distal edge 92 is generally opposite the proximal edge 90 and is remote from the longitudinal centerline 16. The front edge 94 is defined as the edge generally oriented towards the front waist edge 48. The back edge 96 is generally opposite the front edge 94 and is generally oriented towards the back waist edge 46. The back fasteners 44 have a first direction centerline 84 relative to the front edge 94 and the back edge 96 and a second direction centerline 86 relative to the proximal edge 90 and the distal edge 92. The first direction centerline 84 and the second direction centerline 86 intersect at a midpoint 88. The midpoint 88 is extended parallel to the lateral direction 14 to the longitudinal centerline 16. The back fastener offset 58 is the distance from the extended midpoint 88 to the back waist edge 46 at the longitudinal centerline 16.

Fastened Offset

Figure 11:
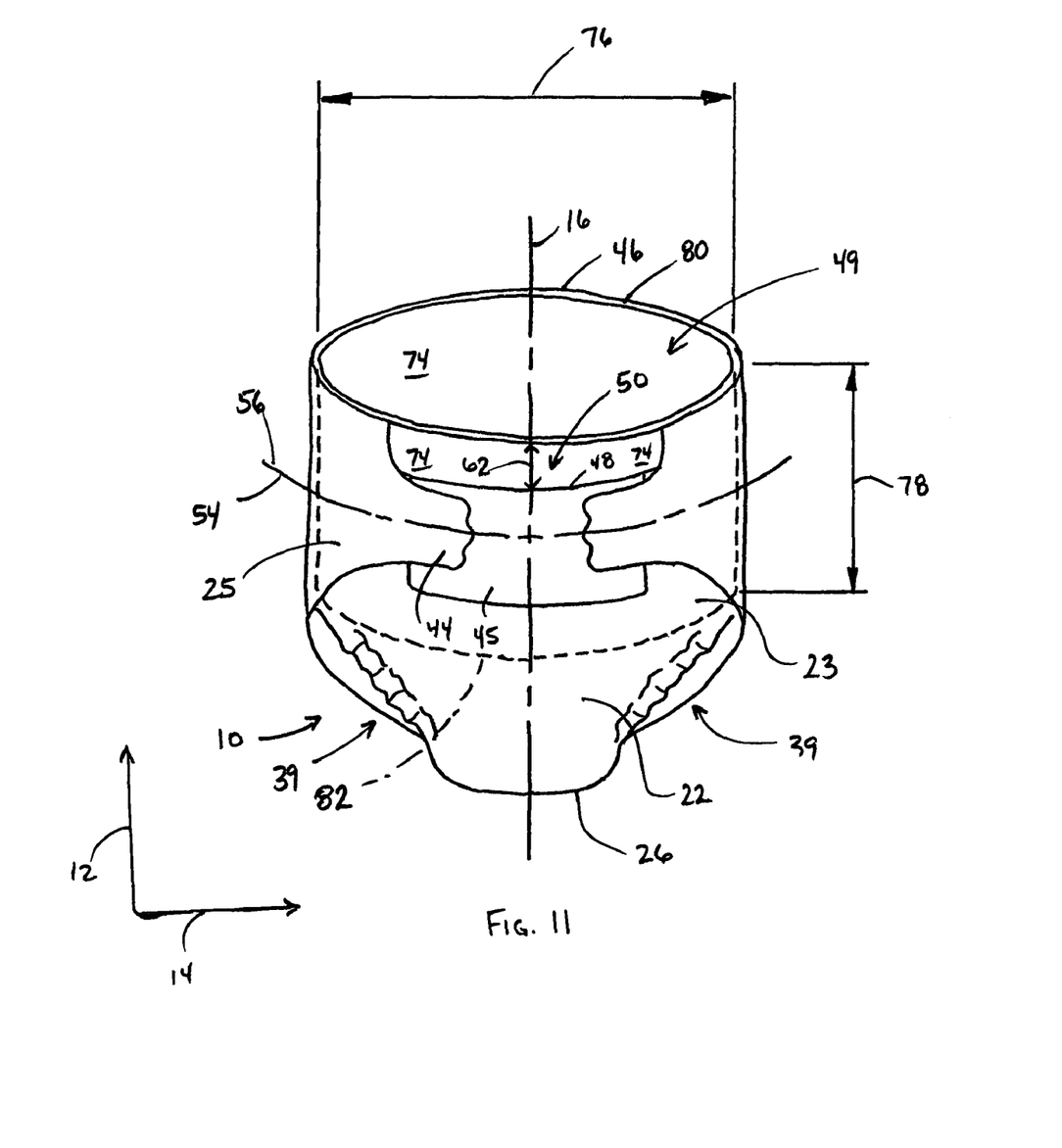
FIG. 11 representatively illustrates an exemplary diaper secured about a cylinder to measure the fastened offset.

The fastened offset 62 is determined by securing a diaper 10 in the fastened condition about a cylinder 74 as illustrated in FIG. 11. The cylinder 74 has an outside diameter 76 of 4 inches (10.16 cm). The cylinder 74 has an upper edge 80 and a lower edge 82. The cylinder 74 has a uniform height 78 around the circumference of the cylinder of 2.5 inches (6.35 cm). The height 78 is the distance between the upper edge 80 and the lower edge 82. The cylinder 74 is constructed of a rigid material capable of preventing deformation under the forces normally applied by a diaper fastener system. For example, the cylinder 74 may be constructed of PVC, metal, plastic, glass, or other similarly rigid materials. The back ears 25 and back fasteners 44 are wrapped around the cylinder 74 and joined with the front fastener 45 located in the front portion 22 to maintain the diaper generally in the position shown. Sufficient force is applied to the back ears 25 such that the diaper 10 remains secured to the cylinder 74 after joining the back fasteners 44 with the front fasteners 45. The force applied should not be so excessive that the back fasteners 44, front fasteners 45 and/or other parts of the diaper 10 are deformed. The back fastener centerline 54 is aligned with and parallel to the front fastener centerline 56. Once fastened around the cylinder 74 as described above, the diaper 10 is manipulated such that the back waist edge 46, at the longitudinal centerline 16, is aligned with the upper edge 80 of the cylinder 74. The fastened offset 62 is the distance from the front waist edge 48, at the longitudinal centerline 16, to the upper edge 80 of the cylinder 74. The fastened offset 62 is defined as positive if the upper edge 80 of the cylinder 74 is extending beyond the front waist edge 48 as illustrated in FIG. 11 when fastened and positioned as described above. The fastened offset 62 is defined as negative if the front waist edge 48 extends beyond the upper edge 80 of the cylinder 74 when fastened and positioned as described above.

Table 1 below includes front fastener offset 60, back fastener offset 58, and fastened offset 62 for various products by way of comparison with the present invention.

TABLE 1

Comparison Measurements

| Product | Back Fastener Offset 58 | Front Fastener Offset 60 | Fastened Offset 62 |
| --- | --- | --- | --- |
| Pampers ® Newborn Swaddlers ™ | 50 mm | 45 mm | 5 mm |
| Pampers ® Swaddlers ™ New Baby | 50 mm | 50 mm | 0 mm |
| HUGGIES ® Newborn diapers | 30 mm | 60 mm | −20 mm |
| Luvs ® Ultra Leakguards ® Newborn diapers | 30 mm | 30 mm | 15 mm |
| Embodiment A of Present Invention | 60 mm | 20 mm | 25 mm |

The Pampers® Newborn Swaddlers™ diapers, The Pampers® Swaddlers™ New Baby diapers and the Luvs® Ultra Leakguards® Newborn diapers were manufactured by Procter & Gamble and were purchased at ShopKo® store #100 located at 699 South Green Bay Road, Neenah, Wis., USA on Mar. 7, 2005.

The HUGGIES® Newborn diapers were manufactured by the Kimberly-Clark Corporation and were the same as those sold in the U.S. in 2005.

While the invention has been described in detail with respect to specific embodiments thereof, it will be appreciated that those skilled in the art, upon attaining an understanding of the foregoing will readily appreciate alterations to, variations of and equivalents to these embodiments. Accordingly, the scope of the present invention should be assessed as that of the appended claims and any equivalents thereto.

The invention claimed is:

1. A diaper having an unfastened condition and a fastened condition, the diaper comprising,
   a. a front portion,
   b. a back portion,
   c. a fastener system adapted to join the back portion to the front portion thereby transitioning the diaper from the unfastened condition to the fastened condition,
   d. the diaper adapted to provide an umbilical relief area when in the fastened condition without tearing or folding the front waist edge,
   e. the diaper not having an umbilical notch when in the unfastened condition.

2. The diaper of claim 1 further comprising a longitudinal centerline, and wherein,
   a. the fastener system comprises a front fastener and a pair of back fasteners, the back fasteners being adapted to join with the front fastener thereby transitioning the diaper from the unfastened condition to the fastened condition,
   b. the front portion has a straight front waist edge at the longitudinal centerline,
   c. the diaper has a fastened offset of at least 15 mm.

3. The diaper of claim 1, wherein,
   a. the fastener system comprises a front fastener and a pair of back fasteners, the back fasteners being adapted to join with the front fastener thereby transitioning the diaper from the unfastened condition to the fastened condition,
   b. the front fastener has a front fastener offset of less than 30 mm and the back fasteners have a back fastener offset of at least 50 mm.

4. The diaper of claim 2, wherein, the front fastener has a front fastener offset of less than 30 mm and the back fasteners have a back fastener offset of at least 50 mm.

5. The diaper of claim 1 further comprising at least one stabilizer joined with the back portion and wherein the back portion includes a back waist edge, the at least one stabilizer being located proximate the back waist edge and adapted to minimize back waist edge rollover.

6. The diaper of claim 1 further comprising at least one stabilizer joined with the front portion and wherein the front portion includes a front waist edge, the at least one stabilizer being located proximate the front waist edge and adapted to minimize front waist edge rollover.

7. A diaper having an unfastened condition, a fastened condition, and a longitudinal centerline, the diaper comprising,
   a. a front portion having a straight front waist edge at the longitudinal centerline and the front portion having at least one front fastener,
   b. a back portion having at least one back fastener,
   c. the at least one back fastener adapted to join with the at least one front fastener thereby transitioning the diaper from the unfastened condition to the fastened condition,
   d. the diaper having a fastened offset of at least 15 mm.

8. The diaper of claim 7 wherein the fastened offset is at least 20 mm.

9. The diaper of claim 7 wherein the fastened offset is at least 25 mm.

10. The diaper of claim 7 wherein the fastened offset is at least 30 mm.

11. The diaper of claim 7 wherein the at least one front fastener has a front fastener offset of less than 30 mm and the at least one back fastener has a back fastener offset of at least 50 mm.

12. The diaper of claim 7 further comprising at least one stabilizer joined with the back portion and wherein the back portion includes a back waist edge, the at least one stabilizer being located proximate the back waist edge and adapted to minimize back waist edge rollover.

13. The diaper of claim 7 further comprising at least one stabilizer joined with the front portion, the at least one stabilizer being located proximate the front waist edge and adapted to minimize front waist edge rollover.

14. A diaper having an unfastened condition and a fastened condition, the diaper comprising,
   a. a front portion,
   b. a back portion,
   c. a fastener system adapted to join the back portion to the front portion thereby transitioning the diaper from the unfastened condition to the fastened condition,
   d. the front portion having a front waist edge and a front fastener, the front fastener having a front fastener offset of less than 30 mm,
   e. the back portion having a back waist edge and a pair of back fasteners, the back fasteners having a back fastener offset of at least 50 mm.

15. The diaper of claim 14 wherein the front fastener offset is less than 25 mm.

16. The diaper of claim 15 wherein the back fastener offset is at least 60 mm.

17. The diaper of claim 14 wherein the back fastener offset is at least 60 mm.

18. The diaper of claim 14 wherein the front fastener offset is less than 20 mm.

19. The diaper of claim 18 wherein the back fastener offset is at least 70 mm.

20. The diaper of claim 14 wherein the back fastener offset is at least 70 mm.

* * * * *